(12) United States Patent
Braunagel et al.

(10) Patent No.: US 12,402,852 B2
(45) Date of Patent: Sep. 2, 2025

(54) X-RAY IMAGING SYSTEM AND METHOD

(71) Applicant: KONINKLIJKE PHILIPS N.V., Eindhoven (NL)

(72) Inventors: Andre Braunagel, Garching (DE); Thomas Koehler, Norderstedt (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 230 days.

(21) Appl. No.: 18/272,873

(22) PCT Filed: Jan. 17, 2022

(86) PCT No.: PCT/EP2022/050873
§ 371 (c)(1),
(2) Date: Jul. 18, 2023

(87) PCT Pub. No.: WO2022/157114
PCT Pub. Date: Jul. 28, 2022

(65) Prior Publication Data
US 2024/0090862 A1 Mar. 21, 2024

(30) Foreign Application Priority Data
Jan. 19, 2021 (EP) .................................... 21152312

(51) Int. Cl.
*A61B 6/00* (2024.01)
*A61B 6/40* (2024.01)
(Continued)

(52) U.S. Cl.
CPC .......... *A61B 6/5235* (2013.01); *A61B 6/4035* (2013.01); *A61B 6/405* (2013.01);
(Continued)

(58) Field of Classification Search
CPC ......... A61B 6/00; A61B 6/4035; A61B 6/405; A61B 6/4291; A61B 6/482; A61B 6/484;
(Continued)

(56) References Cited

U.S. PATENT DOCUMENTS

2013/0170618 A1 7/2013 Koehler
2014/0177789 A1 6/2014 Baturin et al.
(Continued)

FOREIGN PATENT DOCUMENTS

EP 3059579 A1 8/2016
WO WO2014100063 A1 6/2014
WO WO2017191247 A1 11/2017

OTHER PUBLICATIONS

PCT International Search Report, International application No. PCT/EP2022/050873, Apr. 4, 2022.
(Continued)

*Primary Examiner* — Jurie Yun
(74) *Attorney, Agent, or Firm* — Larry Liberchuk

(57) ABSTRACT

Concepts for multi-energy dark-field (DAX) and phase-contrast (PC) X-ray imaging are proposed. One such concept comprise acquiring a set of low energy images with phase stepping and a set of high energy images (with or without phase stepping). Transmission, DAX, and PC images are obtained from the phase-stepped low energy images using phase retrieval. Also, a high energy transmission image is obtained from the high energy image(s). Based on the transmission image from the low energy images and the transmission image from the high energy image(s), a modified transmission image is generated.

15 Claims, 5 Drawing Sheets

(51) Int. Cl.
　　　*A61B 6/42*　　　(2024.01)
　　　*G16H 50/20*　　(2018.01)
(52) U.S. Cl.
　　　CPC ............ *A61B 6/4291* (2013.01); *A61B 6/482* (2013.01); *A61B 6/484* (2013.01); *A61B 6/5258* (2013.01); *G16H 50/20* (2018.01)
(58) Field of Classification Search
　　　CPC ....... A61B 6/50; A61B 6/5235; A61B 6/5258; G16H 50/20
　　　See application file for complete search history.

(56) References Cited

U.S. PATENT DOCUMENTS

| | | |
|---|---|---|
| 2016/0135769 A1 | 5/2016 | Wang et al. |
| 2017/0156686 A1 | 6/2017 | Koehler et al. |

OTHER PUBLICATIONS

Wolf S. et al., "CycleGAN: Learning to Translate Images (Without Paired Training Data)", Towards data Science, Nov. 2018. https://towardsdatascience.com/cyclegan-learning-to-translate-images-without-paired-training-data-5b4e93862c8d.

Welander P. et al., "Generative Adversarial Networks for Image-to-Image Translation on Multi-Contrast MR Images—A Comparison of CycleGAN and UNIT", ArXiv, 2018, vol. abs/1806.07777, https://arxiv.org/abs/1806.07777.

Weitkamp, T. et al., "X-Ray Phase Imaging with a Grating Interferometer", Optics Express, vol. 13, issue 16, pp. 6296-6304, 2005.

X-RAY IMAGING SYSTEM AND METHOD

FIELD OF THE INVENTION

The invention relates to the field of dark-field X-ray imaging and phase contrast X-ray imaging. The invention relates to a multi-energy dark-field and phase-contrast X-ray imaging system, a method of multi-energy dark-field and phase contrast X-ray imaging and a related computer program product.

BACKGROUND OF THE INVENTION

Dark-field X-ray (DAX) imaging has recently demonstrated an improved diagnostic accuracy for the diagnosing and staging of pulmonary disorders. In conventional techniques of X-ray imaging, an object is exposed to X-rays to obtain a transmission image of the object. However, for soft tissues including vessels, cartilages, lungs, and breast tissues with little absorption, this provides poor attenuation contrast compared with bone images. In order to overcome this limitation, there have been major developments in recent years to obtain DAX and phase-contrast (PC) images using X-rays.

Some of the techniques used for DAX and PC imaging can be classified as grating interferometric methods or grating non-interferometric methods. In each of these techniques, a fringe pattern of X-rays is generated after the X-rays have traversed the object. The changes in the fringe pattern induced by the object can be used to extract DAX and PC images.

In DAX and PC imaging, at least partly coherent X-ray radiation is employed, e.g., generated by a source grating arranged adjacent to, in the vicinity of an X-ray source, e.g. an X-ray tube. Coherent X-rays penetrating the object may allow for subsequent retrieval of phase information. To obtain appropriate phase information, a so-called phase stepping is performed.

In phase stepping, one (interference) grating is displaced laterally with respect to another grating(s) and the X-ray detector element by a fraction of its grating pitch, e.g., a fourth, sixth, eighth of the grating pitch, e.g. of the phase grating. If the phase stepping is performed using a particular grating, then the phase stepping shall cover a full period of this particular grating. It has been shown that phase stepping techniques typically require acquisition of ten or even more images in order to sufficiently suppress vibrational disturbances.

In regular transmission images of human patients an X-ray energy of about 125 kVp is used as the ribs have less contrast for high kVp. However, DAX imaging is more sensitive at lower X-ray energies, with X-ray energies of about 70 kVp being used. The ribs become visible at these lower X-ray energies, to the extent that the bones interfere with the ability to analyse and interpret the dark-field and the transmission images at these energies.

One of the advantages of DAX is that it is always acquired alongside a transmission image. The simultaneous acquisition of DAX and transmission images has the disadvantage that acquisition parameters have to be traded-off. In particular, DAX image acquisition is typically optimal for X-ray energies between 60 kVp and 70 kVp since the DAX signal generated by the lung tissue rapidly decreases with increasing X-ray energy. Furthermore, the current medical guidelines state that chest radiography should be performed at energies≥120 kVp, since the ribs have less attenuation contrast for higher kVp.

SUMMARY OF THE INVENTION

The invention is defined by the claims.

According to examples in accordance with an aspect of the invention, there is provided a multi-energy dark-field (DAX) and phase-contrast (PC) X-ray imaging system. The system comprises: an imaging unit configured to acquire a plurality of phase-stepped X-ray images at a first set of energy values and at least one X-ray image at a second set of energy values, wherein each energy value of the first set is less than each energy value of the second set; and a processing unit configured to: process the plurality of phase-stepped X-ray images acquired at the first set of energy values using phase retrieval to obtain a first transmission image, a DAX image, and a PC image; process the at least one X-ray image acquired at the second set of energy values to obtain a second transmission image; and process the first transmission image based on the second transmission image so as to generate a modified transmission image.

The system acquires a set of low energy images with phase stepping and a set of high energy images (with or without phase stepping). Transmission, DAX, and PC images are obtained from the phase-stepped low energy images using phase retrieval. A high energy transmission image is obtained from the high energy image(s).

Based on the transmission image from the low energy images (i.e. first transmission image) and the transmission image from the high energy image(s) (i.e. second transmission image), a modified transmission image is generated.

By being based on the second transmission image, the modified transmission image may retain characteristics (e.g. a high signal-to-noise ratio) of the second transmission image, and therefore appear as though it has been acquired at high energy (e.g. 125 kVp), thereby meeting clinical requirements regarding acquisition energy for X-ray imaging of the thorax.

By also being based on the first transmission image, the modified transmission image may also retain characteristics (e.g. the framing of the image) of the first transmission image. Since the system is able to acquire the low energy DAX and PC images simultaneously to the first transmission image, the low energy DAX and PC images can therefore be directly compared to the modified transmission image, since the framing of the images are all the same (i.e. the images are registered/aligned to one another).

Furthermore, by being based on both the first transmission image and the second transmission image, the high energy transmission image characteristics and low energy transmission image characteristics may be compared (e.g. attenuation contrast). The processing unit may obtain image segmentation information from the comparison and use the information to remove high-absorbing features in the image (e.g. bones), or conversely, remove low-absorbing features in the image (e.g. soft tissue).

By way of example, the modified transmission image may be a combination of the high and low energy transmission images in such a way that the system may reduce noise and/or remove bones or soft tissue in the modified transmission image. The modified transmission image may be matched with a DAX image and/or a PC image with identical subject matter and framing to the first transmission image, and the modified transmission image may be clinically acceptable.

These and other aspects of the invention will be apparent from and elucidated with reference to the embodiment(s) described hereinafter.

In some embodiments, the imaging unit may comprise a grating interferometer, a plurality of (periodal) apertures, a propagating-based imaging arrangement, or a rotating crystal configured to acquire the plurality of phase-stepped X-ray images at the first set of energy values. The phase-stepped image series may be acquired with a variety of hardware: the grating interferometer for grating-based imaging; the plurality of apertures for edge illumination; the propagating sensor for propagation-based imaging; and the rotating crystal for analyser-based imaging. Embodiments utilising different hardware may offer advantages such as, but not limited to, improved system sensitivity for a certain subject, improved phase stepping control, and improved spatial resolution.

In some embodiments, the first set of energy values may consist of energy values less than 100 kVp, and preferably within the range of 60 kVp to 70 kVp. Thus, the phase-stepped image series may be acquired at at least one low energy state for optimal DAX image acquisition between, but not limited to, 60 and 70 kVp.

In some embodiments, the second set of energy values may consist of energy values greater than or equal to 100 kVp, preferably greater than or equal to 120 kVp, and further preferably with at least one energy value substantially equal to 125 kVp. Thus, the at least one X-ray image may be acquired at at least one high energy state for optimal transmission image acquisition above 120 kVp and ideally at 125 kVp.

In some embodiments, the processing unit may be configured to process at least one of the phase-stepped X-ray images and/or the at least one X-ray image according to a fringe removal (e.g. phase-stepping) algorithm so as to remove fringes. Furthermore, in some embodiments, the imaging unit may be configured to process at least one of the phase-stepped X-ray images and/or the at least one X-ray image according to a fringe removal algorithm using an X-ray beam spectrum filter and/or a dynamic interference grating so as to remove residual fringes.

Fringes can arise from acquiring images using a DAX system configured to perform phase stepping with grating interferometry. Embodiments may therefore be configured to remove or reduce such fringes. Embodiments may, for example, acquire a phase-stepped X-ray image with no object present to obtain fringe information. However, information about fringes may be obtained by other methods. The processing unit could then perform the fringe removal algorithm using the fringe information. Some embodiments may use the physical components of the imaging system to remove the fringes, i.e. moving the interference grating to smear the fringes, or prevent them from being created in the first place, i.e. using the spectrum filter. Removal of the fringes increases the contrast, clarity, and overall quality of X-ray images.

In some embodiments, the processing unit may be configured to process the first transmission image based on the second transmission image to reduce noise in the modified transmission image. DAX images acquired at optimal lower energy values are useful for diagnosing pulmonary disorders. However, the transmission images acquired simultaneously at lower energy values have a poor signal-to-noise ratio and are not in line with the medical guidelines. Therefore, the processing unit may improve the signal-to-noise ratio in the low energy transmission images using information from the high energy transmission images, where the resultant modified transmission image may be a 'virtual' 125 kVp image that is clinically acceptable.

In some embodiments, the processing unit may be configured to process the first transmission image based on the second transmission image to remove soft tissue or bones in the modified transmission image. The difference in attenuation contrast for high absorbing features, i.e. bones, between the low and high energy transmission images may be determined using techniques such as image segmentation. The difference may then be used for removal of bones or soft tissue from X-ray images. This may be beneficial in diagnosing pulmonary disorders since there is less irrelevant information in the images for clinicians to process. It may also be used to identify features in the transmission image that might be obscured by the high absorbing features.

In some embodiments, the processing unit is further configured to execute a training algorithm, wherein the training algorithm creates a trained neural network configured to receive training inputs and known outputs, wherein the training inputs comprise the first transmission images and the known outputs comprise the modified transmission images. Furthermore, in some embodiments, the processing unit is further configured to execute an image processing algorithm, wherein the image processing algorithm is configured to use the trained neural network to receive inputs comprising the first transmission images and generate outputs comprising the modified transmission images.

The difference between the first and second transmission images is not extreme and a neural network could be trained to output the modified transmission image from the system without the need for acquiring the second transmission image. In some embodiments of the neural network, it may be trained for noise reduction, bone or soft tissue removal, and/or combination of the previous two effects. These deep learning methods may increase the speed at which the system can output clinically acceptable multi-energy X-ray images. Furthermore, the deep learning methods may simplify the inputs required to the system to perform multi-energy DAX and PC imaging.

According to another aspect of the invention, there is provided a method of multi-energy dark-field (DAX) and phase-contrast (PC) X-ray imaging. The method comprises: acquiring: a plurality of phase-stepped X-ray images at a first set of energy values; and at least one X-ray image at a second set of energy values, wherein each energy value of the first set is less than each energy value of the second set; performing a phase retrieval process on the plurality of phase-stepped X-ray images acquired at the first set of energy values to obtain a first transmission image, a DAX image, and a phase-contrast (PC) image; processing the at least one X-ray image acquired at the second set of energy values to obtain a second transmission image; and processing the first transmission image based on the second transmission image so as to generate a modified transmission image.

In some embodiments, the method wherein processing the first transmission image comprises reducing noise in the first transmission image based on the second transmission image.

Further, in some embodiments, the second transmission image may be used in order to adapt the contrast between different materials (e.g. soft tissue and bones) in the first transmission image. Thus, in some embodiments, the method wherein processing the first transmission image comprises removal of soft tissue or bones from the first transmission image based on the second transmission image.

In some embodiments, the method may consist of the first set of energy values consisting of energy values less than 100 kVp, and preferably within the range of 60 kVp to 70 kVp.

According to another aspect of the invention, there is provided a computer program product comprising computer program code means which, when executed on a computing device having a processing system, cause the processing system to perform all of the steps of the method according to a proposed embodiment.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
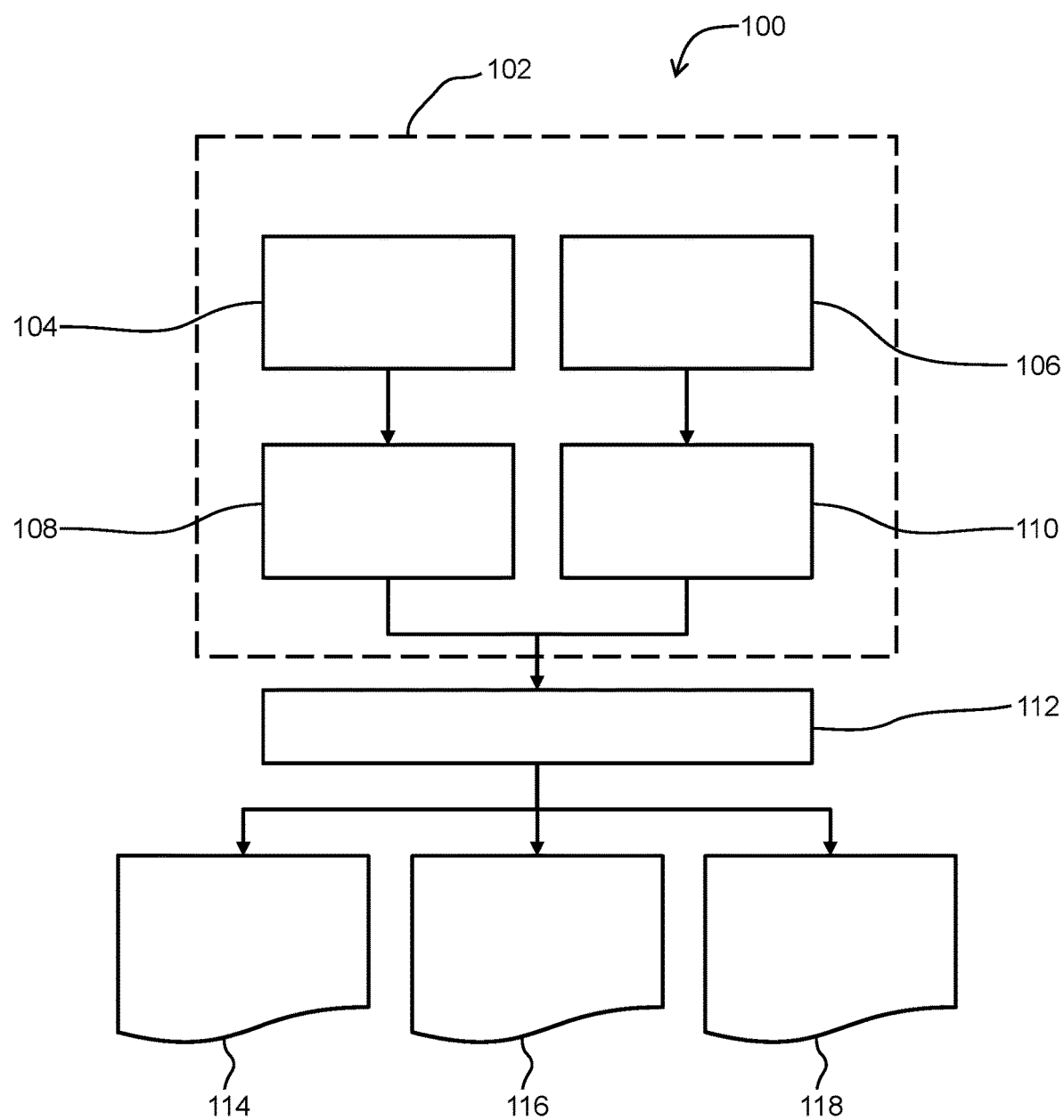
FIG. 1 is a flow diagram of a multi-energy DAX imaging system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

There is proposed a multi-energy dark-field (DAX) and phase-contrast (PC) X-ray imaging system, comprising an imaging unit configured to acquire a plurality of phase-stepped X-ray images at a first set of energy values and at least one X-ray image at a second set of energy values, wherein each energy value of the first set is less than each energy value of the second set. The multi-energy DAX imaging system further comprises a processing unit configured to process the plurality of phase-stepped X-ray images acquired at the first set of energy values using phase retrieval to obtain a first transmission image, a DAX image, and a phase-contrast image. The processing unit is further configured to process the at least one X-ray image acquired at the second set of energy values to obtain a second transmission image, and process the first transmission image based on the second transmission image so as to generate a modified transmission image.

Embodiments may provide a multi-energy dark-field (DAX) and phase-contrast X-ray imaging concept, comprising: acquisition of a series of images with phase stepping at low kVp; acquisition of one (or more) additional image with or without phase stepping at high kVp; phase retrieval of the stepping series at low kVp, resulting in a DAX image and a low kVp transmission image; removal of fringes from the high kVp transmission image; and combination of the transmission images, for instance: de-noising of the high kVp transmission image using additional structure information taken from the low kVp transmission image; and/or state-of the art dual energy combination of the low kVp transmission image and the high kVp transmission image in order to do bone removal or soft-tissue removal. Thus, there is proposed a concept of combining the DAX image acquisition with a multi-energy transmission image acquisition. In general, proposed embodiments are not limited to two energies acquisition only, i.e. in principle, each new step of the phase stepping can be acquired at a different energy. In this case, phase-retrieval is performed taking all the images into account at once, while keeping in mind the influence of the x-ray energy on the visibility (performance) of the grating interferometer.

DAX imaging includes an X-ray source and a configuration that allows for the magnitude of diffraction of X-rays through an object to be measured rather than the attenuation of X-rays through the same object.

Phase stepping in X-ray imaging is a process known to those skilled in the art and includes determining phase information about the object. In particular, phase stepping may be performed by moving a grating laterally with respect to a sensor through a distance equal to the period of the grating. In other examples, phase stepping may be performed by moving a sensor laterally with respect to a grating through a distance equal to the period of the grating. This may be done in steps that are less than the period of the grating, so that, when summing up all the steps together, the total travelled distance is the grating period. In yet further examples, phase stepping may be performed using electromagnetic phase stepping wherein the target of an X-ray beam can be moved using electromagnets after the X-ray beam has been emitted from an X-ray source. The movement of the target of the X-ray beam would be through a distance equal to the period of the (phase) grating and laterally to the sensor.

"Energy" or "energy values" refers to the peak potential, peak voltage, and/or maximum voltage applied across an X-ray tube to produce X-rays and is measured in kVp or peak kilovoltage. A higher kVp results in a greater energy of X-rays being emitted from an X-ray source. For instance, a low energy image refers to an X-ray image acquired at a lower kVp relative to the high energy image, and, conversely, a high energy image refers to an X-ray image acquired at a higher kVp relative to the low energy image. The low energy image will typically have a lower signal-to-noise ratio and lower attenuation contrast for transmission images, whereas the DAX image will have a higher signal-to-noise ratio. The high energy image will typically have a higher signal-to-noise ratio and higher attenuation contrast for transmission images, whereas the DAX image will have a lower signal-to-noise ratio.

Referring to FIG. 1, there is depicted a simplified block diagram of a multi-energy DAX and PC X-ray imaging system 100 according to an embodiment. The system comprises an imaging unit 102 and a processing unit 112.

The imaging unit 102 is configured to acquire a plurality of phase-stepped X-ray images 108 at a first set 104 of energy values and at least one X-ray image 110 at a second set 106 of energy values, wherein each energy value of the first set 104 is less than each energy value of the second set 106.

By way of example, the first set 104 of energy values consists of energy values less than 100 kVp (i.e. low energy values), and preferably within the range of 60 kVp to 70 kVp. In this way, the first set 104 of energy values may be configured for optimal acquisition of the DAX image 114. Optimal acquisition of the DAX image 114 may be when the signal-to-noise ratio is greatest. The first set 104 of energy values may be determined automatically, determined by a clinician, or determined by a default value for optimal acquisition of the DAX image 114.

The second set 106 of energy values consists of energy values greater than or equal to 100 kVp (i.e. high energy values), preferably greater than or equal to 120 kVp, and further preferably with at least one energy value substantially equal to 125 kVp (e.g. 125 kVp±1%, or equal to 125 kVp). In this way, the second set 106 of energy values may be configured for optimal acquisition of the second transmission image 416. Optimal acquisition of the second transmission image 416 may be when the signal-to-noise ratio is greatest and/or when the second set 106 energy values are in line with medical guidelines i.e. greater than 120 kVp. The second set 106 of energy values may be determined automatically, determined by a clinician, or determined by a default value for optimal acquisition of the second transmission image 416.

The imaging unit 102, is further configured to provide the plurality of phase-stepped X-ray images 108 at the first set 104 of energy values and the at least one X-ray image 110 at the second set 106 of energy values to the processing unit 112.

The processing unit 112 is configured to process the plurality of phase-stepped X-ray images acquired at the first set of energy values using phase retrieval, so as to obtain a first transmission image, a DAX image 114, and a phase-contrast (PC) image 116. Phase retrieval in DAX imaging is a process known to those skilled in the art and includes determining phase information from X-ray images obtained by phase stepping. In particular, the phase of an X-ray beam may not be measured directly, and a phase-shift is required to be converted to an intensity modulation by interfering two or more waves. Phase retrieval may refer to the implementation of algorithm(s) that perform phase retrieval. The first transmission image 108 is a low energy transmission image 204, and the DAX image 114 and the PC image 116 are both low energy X-ray images.

The processing unit 112 is also configured to process the at least one X-ray image 110 acquired at the second set 106 of energy values to obtain the second transmission image 416. Thus, the second transmission image 416 is a high energy transmission image 206.

The processing unit 112 is yet further configured to process the first transmission image 108 based on the second transmission image 416 so as to generate a modified transmission image 118. In other words, the modified transmission image 118 is a combination of the first transmission image 108 and the second transmission image 416. In other words, the modified transmission image 118 is a combination of the low energy transmission image 204 and the high energy transmission image 206.

The output of the processing unit 112 is the DAX image 114, the PC image 116, and/or the modified transmission image 118, wherein all three outputs are in an optimal state.

The processing unit 112 may be further configured to process the first transmission image 108 based on the second transmission image 410 to reduce noise in the modified transmission image 118. The processing unit 112 determines what an optimal signal-to-noise ratio in a transmission image should be based on the second transmission image 410, i.e. the high energy transmission image 206, since the second transmission image 410 has a high signal-to-noise ratio and is clinically acceptable. The processing unit 112 then uses the contrast information from the second transmission image 410 to process the first transmission image 108, i.e. the low energy transmission image 204, which has a low signal-to-noise ratio and is not clinically acceptable. The processing unit 112 then generates the modified transmission image 118 which has the framing of the first transmission image 108, but with the high signal-to-noise ratio and clinical acceptability of the second transmission image 410.

In some implementations of the system of FIG. 1, the processing unit 112 may be further configured to process the first transmission image 108 based on the second transmission image 410 to remove soft tissue or bones in the modified transmission image 418. The processing unit 112 determines contrast information from the first transmission image 108 and from the second transmission image 410. The contrast information indicates which areas of an image are high absorbing features, i.e. bones. The processing unit 112 may use image segmentation methods to determine contrast information in the first transmission image 108 and the second transmission image 410. The contrast information may be based on any X-ray image information passed to the processing unit 112. The processing unit 112, once the areas of the images are identified as high absorbing features, may then proceed to remove these features. The removal of the features could be done by applying any of the following effects to the determined areas: an opaque mask; a partial opacity mask; lowering the brightness; and/or lowering the contrast.

The processing unit 112 is configured to process at least one of the phase-stepped X-ray images 108 and/or the at least one X-ray image 110 according to a fringe removal algorithm so as to remove fringes. Fringes are artefacts that remain in X-ray images as a result of using grating interferometry and may appear as vertical bands or stripes on X-ray images. The fringe removal algorithm may use a phase-stepped X-ray image with no object present to obtain fringe information, this is not intended to be limiting. The processing unit could then perform the fringe removal algorithm using the fringe information obtained by any method. Removal of the fringes increases the contrast, clarity, and overall quality of X-ray images.

Figure 2:
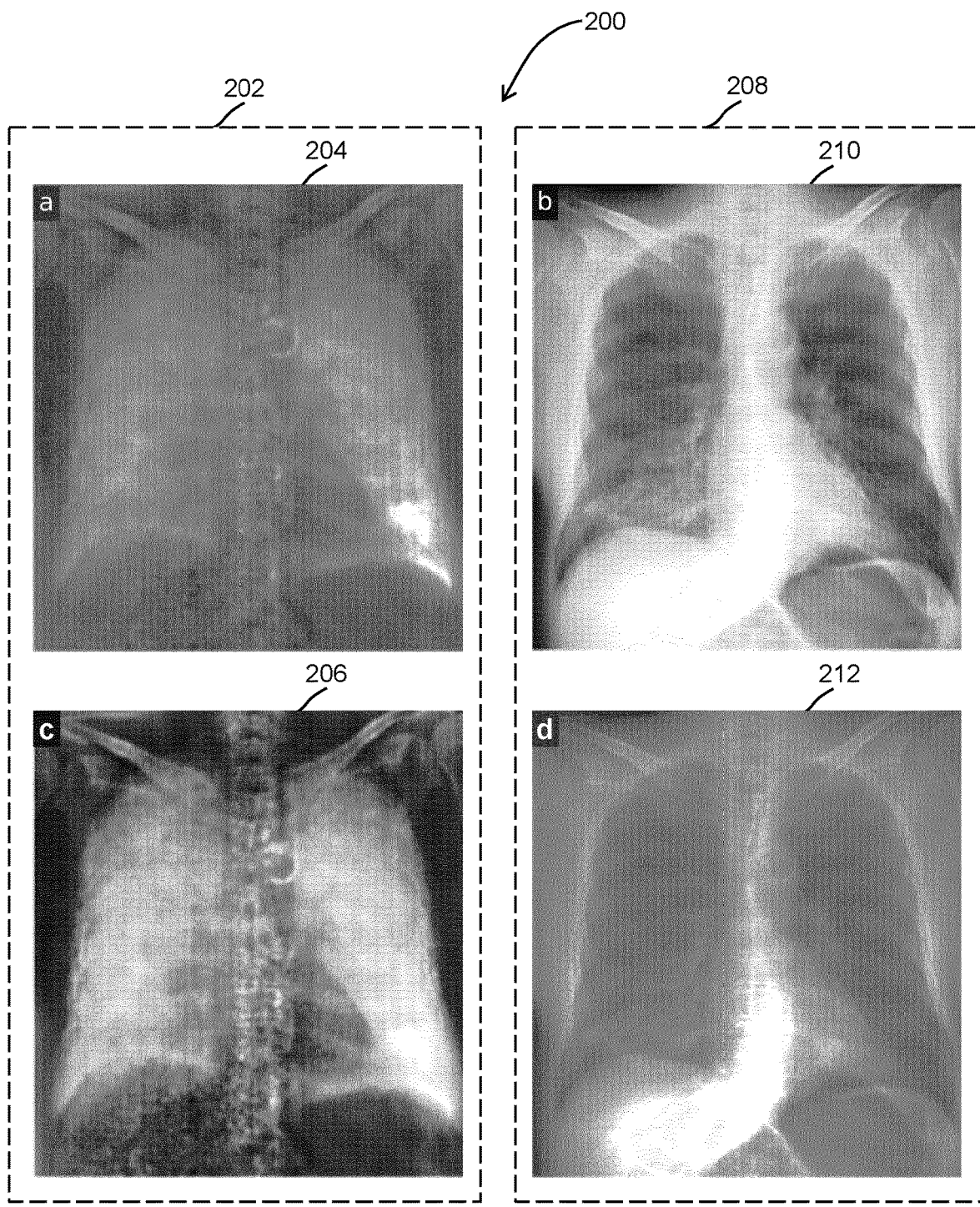
FIG. 2 is an example of transmission X-ray images and an example of dark-field X-ray images.

Referring to FIG. 2, there is depicted an example of a transmission image 202 acquired at low energy 204 and high energy 206, and an example of a DAX image 208 acquired at low energy 210 and high energy 212.

The transmission image 202 is generated from an X-ray signal that has been transmitted through an object 308 and thus the X-ray beam 306 has been attenuated and/or absorbed by the object 308. Energy has been transferred from the X-ray beam 306 into the object 308 and in features that have high absorption properties, typically dense features such as bones, more energy has been transferred and thus the X-ray signal is weaker. This is depicted by the portions of the transmission image 202 where the image appears more white, indicating that more absorption has occurred in that region of the X-ray signal. The transmission image 202 is, by way of example, useful for inspecting for breaks or signs of degradation in high-absorbing features of the object 308 such as bones. A high energy 106 X-ray signal is absorbed more readily into the high-absorbing features when compared to a low energy 104 X-ray signal. Thus, the high energy transmission image 206 has more contrast between the low-absorbing and high-absorbing features of the object 308, known as attenuation contrast. Conversely, the low energy transmission image 204 will have less attenuation contrast between the low-absorbing and high-absorbing features.

The DAX image 208 is generated from an X-ray signal that has been diffracted through an object 308 and thus the phase of the X-ray beam 306 has changed. Diffraction of the X-ray beam 306 is governed by small-angle scattering, thus the magnitude of diffraction will be different through features of the object 308 that have different electron densities. Therefore, the DAX image 208 is better at capturing information from low-absorbing features of the object 308, such as soft tissue. The diffraction information from the high energy 106 X-ray signal deteriorates more quickly through the object 308 compared to the low energy 104 X-ray signal. Thus, the low energy DAX image 212 has more contrast between the small changes in electron densities in soft tissues of the object 308 (when compared to the high energy DAX image). Conversely, the high energy DAX image 210 has less contrast between the small changes in electron densities in soft tissues of the object 308.

In X-ray imaging of the human thorax, the soft tissue is of greater interest than the bones for diagnosis of pulmonary disorders. Thus, the DAX image 208 is useful to clinicians, but needs to be matched with the transmission image 202, for example to be clinically acceptable. The transmission image 202 can be obtained simultaneously to the DAX image 208 on a DAX imaging system, through phase retrieval 406. However, as described previously there is a trade-off in the acquisition parameters of the two images, wherein the transmission image 202 is best acquired at high energies 106, and the DAX image is best acquired at low energies 104.

However, according to the proposed concept(s), a modified transmission image may be provided which retains characteristics of low energy acquisition whilst appearing as though it has been acquired at high energy (e.g. 125 kVp), thereby meeting clinical requirements regarding acquisition energy for X-ray imaging of the thorax for example.

Figure 3:
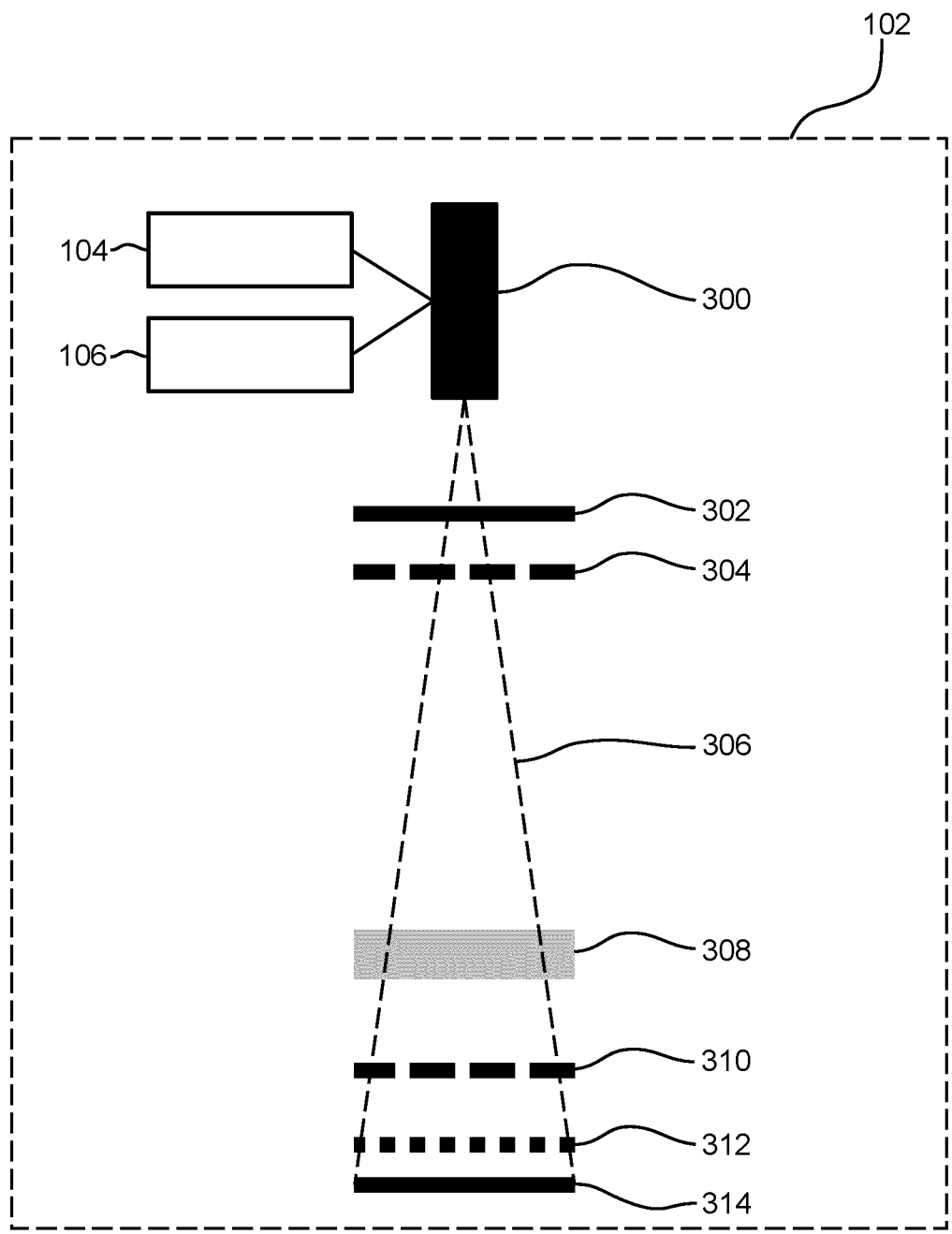
FIG. 3 is a schematic representation of an imaging unit, according to one or more embodiments of the invention.

By way of further illustration, an exemplary imaging unit 102 that may be employed according to proposed embodiments will now be described with reference to FIG. 3. FIG. 3 depicts a simplified schematic of the imaging unit 102 according to an embodiment. Specifically, in this embodiment, the imaging unit 102 comprises a grating interferometer 304, 310, 312 configured to acquire the plurality of phase-stepped X-ray images 108 at the first set 104 of energy values.

The imaging unit 102 comprises an X-ray source 300, an X-ray beam spectrum filter 302, a source grating 304, an X-ray beam 306, an object 308, a phase grating 310, an analyser grating 312, and/or a sensor 314.

The source grating 304, the phase grating 310, and/or the analyser grating 312 may be configured in accordance with the configuration of the first set 104 of energy values, the second set 106 of energy values, and/or the X-ray source 300. In other words, in some embodiments, the distance between any of the gratings 304, 310, 312, may be modified to suit the energy levels of the X-ray beam 306 as it passes through the gratings 304, 310, 312 in order to maximise quality of phase information in the phase-stepped X-ray images 108 and/or signal-to-noise ratio in the phase-stepped X-ray images 108 and/or the at least one X-ray image 110.

The imaging unit comprises a grating interferometer 304, 310, 312 configured to acquire the plurality of phase-stepped X-ray images 108 at the first set 104 of energy values. The grating interferometer set up comprises a phase grating 310 and an analyser grating 312, and additionally may comprise a source grating 304. The gratings comprise a repeating structure of a line of a first material, and a line of a second material or empty space. Thus the gratings have an alternating line structure. The gratings have key dimensions such as the period, which is the perpendicular distance between the edge of a line of the first material and the edge of the next line of the first material. The period of the gratings is determined to suit different energy values 104, 106 of the X-ray beam 306. Another key dimension of the gratings is the distance between the phase grating 310 and the analyser grating 312 which is also determined to suit the energy vales 104, 106 of the X-ray beam 306.

As a phase of a wave may not be measured directly, rather a phase-shift is required to be converted to an intensity modulation by interfering two or more waves. For generating a corresponding interference pattern, the phase grating 310 is employed, which is arranged between the object 308 to be examined and the sensor 314 (alternatively, it may be arranged between the source grating 304 and the object 308). As the interference pattern generated by the phase grating 310 may be too small to be detectable with the sensor 314, due to a lack of spatial resolution of the sensor 314, the analyser grating 312 is arranged between the phase grating 310 and the sensor 314 for subsequently providing an interference pattern, which is large enough to be detectable by the sensor 314. Preferably, introduction of the analyser 312 grating does not introduce any new fringes, but it is just used to "analyse" the interference pattern of the phase grating 310.

Phase stepping is performed by moving the analyser grating 312 perpendicularly with respect to the direction of the line gratings of the analyser grating 312 and in steps that together result in a total distance equal to the period of the analyser grating 312. The phase-stepped X-ray images 108 are acquired by the sensor at a plurality of instances (i.e. different steps) wherein the instances are at a fraction, e.g. a fourth, a sixth, an eighth, of the period of the analyser grating 312, i.e. the distance equal to the period of the analyser grating 312. The plurality of instances are required to obtain an image series from which phase information can be obtained. The analyser grating 312 may be moved by implementing a motor, or any actuator with the precision to achieve the fractional accuracy of the period. Phase stepping may require acquisition of ten or even more images in order to suppress vibrational disturbances.

Alternatively, by way of example, phase stepping may be performed by:
  (i) moving the sensor 314 perpendicularly with respect to the direction of the line gratings of the analyser grating 312;
  (ii) moving a grating perpendicularly with respect to the direction of the line gratings of the analyser grating 312;
  (iii) moving the X-ray source 300 perpendicularly with respect to the direction of the line gratings of the analyser grating 312;
  (iv) moving the X-ray beam 306 perpendicularly with respect to the direction of the line gratings of the analyser grating 312 i.e. by using electromagnetic phase stepping; and
  (v) rotating the phase grating 310 and analyser grating 312 together around an axis along the orientation of grating bars by an angle (e.g. the two gratings are kept in an aligned position with respect to each other or are fixed together mechanically).

In order to obtain the effect of phase stepping by other means, the function of the grating interferometry in the imaging unit may be replaced with:
- an X-ray mask for the sensor 314 with a plurality of apertures in the X-ray mask, i.e. a coded aperture, for edge illumination;
- a propagating sensor that can move parallel to the direction of the X-ray beam 306; or
- a rotating crystal configured to direct the X-ray beam after it has passed through the object 308 over the sensor 314.

The imaging unit may comprise an X-ray beam spectrum filter 302 and/or a dynamic interference grating 304, wherein the X-ray beam spectrum filter 302 and/or a dynamic interference grating 304 are configured to remove fringes from at least one of the phase-stepped X-ray images 108 and/or the at least one X-ray image 110. The X-ray beam spectrum filter 302 may prevent the fringes from being created in the first place by ensuring the X-ray beam 306 is of sufficient quality to not create fringes. The dynamic interference grating 304 may be configured to move the interference grating during image acquisition to smear the fringes out of the resultant images. Removal of the fringes increases the contrast, clarity, and overall quality of X-ray images.

Figure 4:
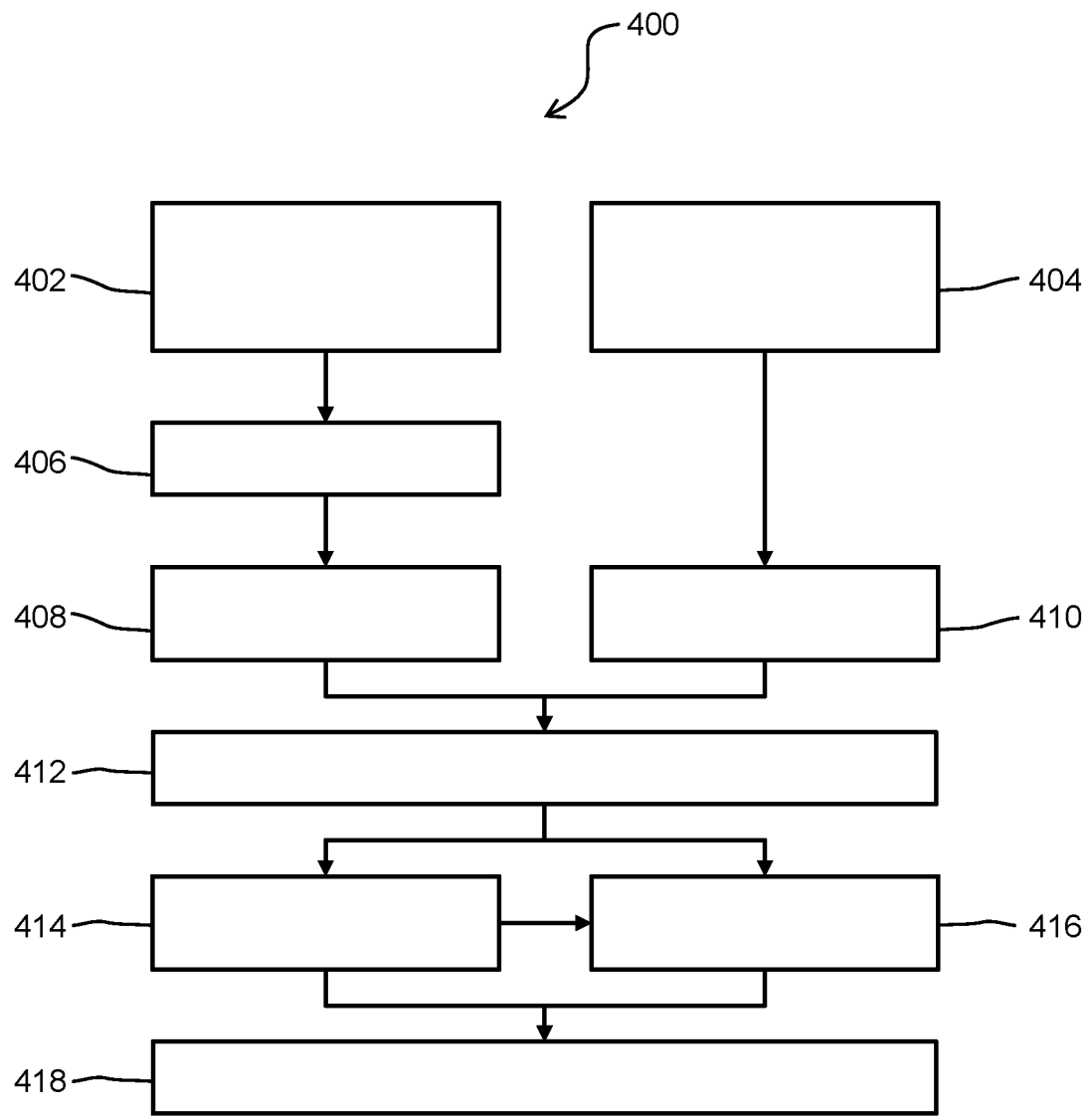
FIG. 4 is a flow diagram of a method for multi-energy DAX imaging, according to one or more embodiments of the invention.

Referring to FIG. 4, there is depicted a simplified block diagram of a method 400 for multi-energy DAX and PC X-ray imaging according to an embodiment. Specifically, in this embodiment, the processing unit 112 is configured to carry out the steps of the method 400.

At steps 402 and 404, the method 400 receives a plurality of phase-stepped X-ray images that have been acquired at a first set 104 of energy values and an at least one X-ray image (with or without phase stepping) that has been acquired at a second set 106 of energy values, wherein each energy value of the first set is less than each energy value of the second set.

By way of example, the first set 104 of energy values consists of energy values less than 100 kVp (i.e. low energy values), and preferably within the range of 60 kVp to 70 kVp. The first set 104 of energy values may be determined automatically by the processing unit 112 or otherwise, determined by a clinician, or determined by a default value for optimal acquisition of the DAX image 114.

The second set 106 of energy values consists of energy values greater than or equal to 100 kVp (i.e. high energy values), preferably greater than or equal to 120 kVp, and further preferably with at least one energy value substantially equal to 125 kVp. The second set 106 of energy values may be determined automatically, determined by a clinician, or determined by a default value for optimal acquisition of the second transmission image 416.

At step 406, phase retrieval is performed on the plurality of phase-stepped X-ray images from step 402.

At step 408, the outputs of the phase retrieval 406 process are an obtained first transmission image, DAX image, and PC image. The DAX image and the PC image are an output of the method.

At step 410, the received at least one X-ray image from step 404 is processed to obtain a second transmission image.

At step 412, an image combination application processes the first transmission image from step 408 and the second transmission image from step 410. The image combination application determines contrast information from the first transmission image from step 408 and the second transmission image from step 410. The contrast information includes an optimal signal-to-noise ratio in a transmission image and is determined based on the second transmission image 410, since the second transmission image 410 has been acquired at high energy values and therefore has a high signal-to-noise ratio and is clinically acceptable. The contrast information also indicates which areas of an image are high absorbing features, i.e. bones, both in the first transmission image and the second transmission image. The method may use image segmentation methods to determine contrast information.

At step 414, the first transmission image from the image combination application 412 is processed based on the contrast information to reduce and/or remove noise from the first transmission image and a reduced noise image is generated.

At step 416, the first transmission image from the image combination application 412 or the reduced noise image from step 414 is processed based on the contrast information to remove bones or soft tissue from the first transmission image or the reduced noise image. The removal of bones or soft tissue may be done by applying any of the following effects to the determined areas: an opaque mask; a partial opacity mask; lowering the brightness; and/or lowering the contrast. A feature-removed image is generated.

At step 418, a modified transmission image is generated based on the reduced noise image from step 414 or the featured-removed image from step 416. The modified transmission image is an output of the method.

The method 400, may use a computer program product comprising computer program code means which, when executed on a computing device having a processing system, cause the processing system to perform all of the steps of the method 400.

Figure 5:
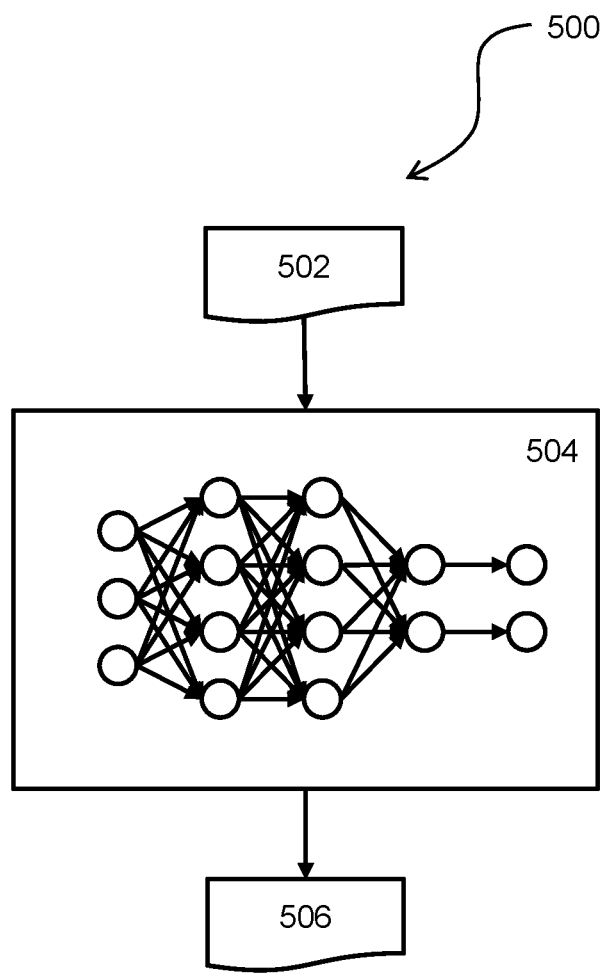
FIG. 5 is a flow diagram of an image processing algorithm configured to use a trained neural network to output modified X-ray images.

Referring to FIG. 5, there is depicted a simplified block diagram of an image processing algorithm 500 according to an embodiment. Specifically, in this embodiment, the processing unit 112 may be configured to carry out the steps of the image processing algorithm 500.

The processing unit 112 may be further configured to execute an image processing algorithm 500, wherein the image processing algorithm is configured to use a trained neural network 504 to receive inputs 502 comprising the first transmission images and generate outputs 506 comprising the modified transmission images. Since the difference in image appearance between 70 kVp and 125 kVp is not extremely high, in particular, only high absorbing parts of the thorax such as the ribcage appear more distinctly on the image, a neural network could be trained on these differences would perform quite well and yield images suitable for diagnostic purposes.

The structure of an artificial neural network (or, simply, neural network) is inspired by the human brain. Neural networks are comprised of layers, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

There are several types of neural network, such as convolutional neural networks (CNNs) and recurrent neural networks (RNNs). Embodiments of the present invention may employ CNN-based learning algorithms, as CNNs have proved to be particularly successful at analyzing images, and are able to classify images with a much lower error rate than other types of neural network.

CNNs typically contain several layers, including a convolutional layer, a pooling layer, a fully connected layer and a softmax layer. The convolutional layer consists of a set of learnable filters and extracts features from the input. The pooling layer is a form of non-linear down-sampling, reducing the data size by combining the outputs of a plurality of neurons in one layer into a single neuron in the next layer. The fully connected layer connects each neuron in one layer to all the neurons in the next layer. The softmax layer determines a probability distribution for each output.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can be repeated until the error converges, and the predicted output data entries are sufficiently similar (e.g. ±1%) to the training output data entries. This is commonly known as a supervised learning technique.

For example, weightings of the mathematical operation of each neuron may be modified until the error converges. Known methods of modifying a neural network include gradient descent, backpropagation algorithms and so on.

The training input data entries for the neural network used in FIG. 5 correspond to example transmission images 408. The training output data entries correspond to modified transmission images 418.

Several pre-processing methods may be employed to improve the training sample. Transmission images from the same imaging system may be normalized in display features for example.

The plurality of neural network may be produced by modifying one or more existing CNN-based learning algorithms, such as VGG, Inception and ResNet for example.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfil the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted that the term "adapted to" is intended to be equivalent to the term "configured to".

Any reference signs in the claims should not be construed as limiting the scope.

The invention claimed is:

1. A multi-energy dark-field (DAX) and phase-contrast (PC) X-ray imaging system, comprising:
   an imager configured to acquire a plurality of phase-stepped X-ray images at a first set of energy values and at least one X-ray image at a second set of energy values, wherein each energy value of the first set is less than each energy value of the second set; and
   a processor configured to:
      process the plurality of phase-stepped X-ray images acquired at the first set of energy values using phase retrieval to obtain a first transmission image, a DAX image, and a phase-contrast (PC) image;
      process the at least one X-ray image acquired at the second set of energy values to obtain a second transmission image; and
      process the first transmission image based on the second transmission image to generate a modified transmission image.

2. The system of claim 1, wherein the imager comprises at least one of a grating interferometer, a plurality of apertures, a propagating-based imaging arrangement, and a rotating crystal configured to acquire the plurality of phase-stepped X-ray images at the first set of energy values.

3. The system of claim 1, wherein the first set of energy values are less than 100 kVp.

4. The system of claim 1, wherein the second set of energy values are greater than or equal to 100 kVp.

5. The system of claim 1, wherein the processor is configured to process at least one of the phase-stepped X-ray images and/or the at least one X-ray image according to a fringe removal algorithm in order to remove fringes.

6. The system of claim 1, wherein the imager further comprises an X-ray beam spectrum filter and/or a dynamic interference grating, wherein the X-ray beam spectrum filter and/or a dynamic interference grating are configured to remove fringes from at least one of the phase-stepped X-ray images and/or the at least one X-ray image.

7. The system of claim 1, wherein the processor is further configured to process the first transmission image based on the second transmission image to reduce noise in the modified transmission image.

8. The system of claim 1 wherein the processor is further configured to process the first transmission image based on the second transmission image to remove soft tissue or bones in the modified transmission image.

9. The system of claim 1, wherein the processor is further configured to execute a training algorithm, wherein the training algorithm creates a trained neural network configured to receive training inputs and known outputs, wherein the training inputs comprise the first transmission images and the known outputs comprise the modified transmission images.

10. The system of claim 9, wherein the processor is further configured to execute an image processing algorithm, wherein the image processing algorithm is configured to use the trained neural network to receive inputs comprising the first transmission images and generate outputs comprising the modified transmission images.

11. A method of multi-energy dark-field (DAX) and phase-contrast (PC) X-ray imaging, comprising:
   acquiring a plurality of phase-stepped X-ray images at a first set of energy values and at least one X-ray image at a second set of energy values, wherein each energy value of the first set is less than each energy value of the second set;

performing a phase retrieval process on the plurality of phase-stepped X-ray images acquired at the first set of energy values to obtain a first transmission image, a DAX image, and a phase-contrast image;

processing the at least one X-ray image acquired at the second set of energy values to obtain a second transmission image; and processing the first transmission image based on the second transmission image-se as to generate a modified transmission image.

12. The method of claim 11, wherein processing the first transmission image comprises reducing noise in the first transmission image based on the second transmission image.

13. The method of claim 11, wherein processing the first transmission image comprises removal of soft tissue or bones from the first transmission image based on the second transmission image.

14. The method of claim 11, wherein the first set of energy values are less than 100 kVp.

15. A non-transitory computer-readable medium for storing executable instructions, which cause a method of multi-energy dark-field (DAX) and phase-contrast (PC) X-ray imaging to be performed, the method comprising:

acquiring a plurality of phase-stepped X-ray images at a first set of energy values and at least one X-ray image at a second set of energy values, wherein each energy value of the first set is less than each energy value of the second set;

performing a phase retrieval process on the plurality of phase-stepped X-ray images acquired at the first set of energy values to obtain a first transmission image, a DAX image, and a phase-contrast image;

processing the at least one X-ray image acquired at the second set of energy values to obtain a second transmission image; and processing the first transmission image based on the second transmission image to generate a modified transmission image.

\* \* \* \* \*